US011090076B2

(12) United States Patent
Walberg et al.

(10) Patent No.: US 11,090,076 B2
(45) Date of Patent: Aug. 17, 2021

(54) SURGICAL INSTRUMENT WITH A COUPLING MECHANISM FOR DRIVING A CUTTING ELEMENT

(71) Applicant: AESCULAP AG, Tuttlingen (DE)

(72) Inventors: Erik Walberg, Tuttlingen (DE); Eugen Herner, Villingen-Schwenningen (DE)

(73) Assignee: AESCULAP AG, Tuttlingen (DE)

(*) Notice: Subject to any disclaimer, the term of this patent is extended or adjusted under 35 U.S.C. 154(b) by 171 days.

(21) Appl. No.: 16/489,891

(22) PCT Filed: Mar. 7, 2018

(86) PCT No.: PCT/EP2018/055634
§ 371 (c)(1),
(2) Date: Aug. 29, 2019

(87) PCT Pub. No.: WO2018/162569
PCT Pub. Date: Sep. 13, 2018

(65) Prior Publication Data
US 2020/0008831 A1 Jan. 9, 2020

(30) Foreign Application Priority Data
Mar. 8, 2017 (DE) .......................... 102017104849.9

(51) Int. Cl.
*A61B 17/32* (2006.01)
*A61B 17/00* (2006.01)

(52) U.S. Cl.
CPC .............. *A61B 17/320016* (2013.01); *A61B 2017/0042* (2013.01); *A61B 2017/00407* (2013.01)

(58) Field of Classification Search
CPC ........ A61F 2/011; A61F 2/2436; A61F 2/962; A61F 2/966; A61B 2018/1452;
(Continued)

(56) References Cited

U.S. PATENT DOCUMENTS 10,123,834 B2 11/2018 Schiele et al.
2011/0087208 A1 4/2011 Boudreaux et al.
(Continued)

FOREIGN PATENT DOCUMENTS

CN 204581463 U 8/2015
DE 202004010313 U1 10/2004
(Continued)

OTHER PUBLICATIONS

German Search Report for German Application No. 10 2017 104 849.9, with English translation, dated Dec. 21, 2017—15 pages.
(Continued)

*Primary Examiner* — Wade Miles

(57) ABSTRACT

A surgical instrument includes a shaft portion which at least partly houses an axially movable cutting element. A handle receives the shaft portion. A trigger element for the cutting element is movably arranged on the handle. The instrument also includes a coupling mechanism which converts a rotation of the trigger element into an axial movement of the cutting element with the interposition of a pinion. The coupling mechanism is designed such that the rotation of the trigger element produces a rotation of the pinion about the central axis thereof and additionally an axial movement of the central axis.

10 Claims, 3 Drawing Sheets

(58) Field of Classification Search
CPC .... A61B 2018/1455; A61B 2018/1457; A61B 2018/146; A61B 2017/0042; A61B 2017/00367; A61B 2017/00407; A61B 2017/2923; A61B 5/15132; A61B 17/320016; A61B 2017/320032
See application file for complete search history.

(56) References Cited

U.S. PATENT DOCUMENTS

| | | | |
|---|---|---|---|
| 2011/0245825 | A1 | 10/2011 | Mitzlaff et al. |
| 2011/0276049 | A1* | 11/2011 | Gerhardt ............ A61B 18/1402 |
| | | | 606/45 |
| 2015/0073394 | A1 | 3/2015 | Schiele et al. |
| 2016/0074105 | A1 | 3/2016 | Garrison |
| 2016/0158049 | A1* | 6/2016 | Dooley .................... A61F 2/95 |
| | | | 606/108 |

FOREIGN PATENT DOCUMENTS

| | | |
|---|---|---|
| DE | 102010016291 A1 | 10/2011 |
| EP | 1621142 A2 | 2/2006 |
| EP | 2845549 A1 | 3/2015 |
| EP | 2845551 A1 | 3/2015 |

OTHER PUBLICATIONS

International Search Report and Written Opinion for International Application No. PCT/EP2018/055634, dated Jun. 6, 2018—8 pages.

* cited by examiner

SURGICAL INSTRUMENT WITH A COUPLING MECHANISM FOR DRIVING A CUTTING ELEMENT

CROSS REFERENCE TO RELATED APPLICATION(S)

This application is the United States national phase entry of International Application No. PCT/EP2018/055634, filed Mar. 7, 2018, which claims the benefit of priority of German Application No. 10 2017 104 849.9, filed Mar. 8, 2017. The contents of International Application No. PCT/EP2018/055634 and German Application No. 10 2017 104 849.9 are incorporated by reference herein in their entireties.

FIELD

The present invention relates to a surgical instrument, for example in the form of a bipolar seal & cut (S&C) instrument of the TFT design (TFT stands for "THERMAL FUSION TECHNOLOGY"), viz. a sealing and cutting instrument. This surgical instrument has a shaft portion which at its distal end area at least partly houses/supports an axially movable cutting element. Further, a handle in which a coupling mechanism converts a trigger movement carried out by a user such as a surgeon at a trigger element (handle) into an axial cutting movement of the cutting element is arranged at the surgical instrument.

BACKGROUND

In minimally invasive surgery and in endoscopy space and weight optimizing plays an important role. Therefore, a space and weight saving configuration has to be ensured not only at the distal instrument head but also at the proximal instrument handle actuated by the user.

Generic surgical instruments have, in their proximal instrument handle, a mechanism for producing a travel path of the cutting element, the so-called coupling mechanism, so that a linear cut can be carried out at a patient by the cutting element. The coupling mechanism thus converts the movement produced by the trigger element, preferably in the form of rotation, into a linear movement, viz. an axial movement, of the cutting element.

Accordingly, low-friction compact and reliable force transmission from the trigger element to the cutting element is essential to meet the high requirements to the precision and the service life of surgical instruments.

From the German Utility Model DE 20 2004 010 313 U1, a surgical instrument comprising a handle on which a trigger element is arranged is known. The partial rotation of the trigger element produced by a user is converted into partial rotation about a different axis via a coupling mechanism not described in greater detail.

Further, surgical instruments comprising coupling mechanisms that are operable by a lever or a cam and produce a linear movement of a cutting element by means of a conventional gear system or pawl mechanism are known from the prior art. Usually plural similar actuations of the trigger element are necessary to carry out a complete cut.

Further coupling mechanisms are realized by means of a pinion-rack combination. They are especially advantageous to reliably transfer rotation to translation. In this case, the trigger element is coupled either to a first rack or directly to the pinion rigidly disposed in the handle so as to transfer a movement to another rack. The further rack in turn is rigidly coupled to the cutting element.

It is a drawback of the prior art that, with an increasing length of the cut to be made by the cutting element, more space is occupied in the instrument handle by the coupling mechanism, as the largest possible travel path of the cutting element corresponds approximately to the length of the coupling mechanism. This conflicts with the target of optimizing space and/or weight.

Further generic prior art is known from the documents DE 20 2004 010 313 U1, DE 2010 016 291 A1 and EP 2 845 551 A1.

SUMMARY

In view of said prior art, the present invention is based on the object to eliminate or at least alleviate the drawbacks of the prior art and especially to disclose a surgical instrument of the generic type (especially operating according to the TFT principle) which enables long travel paths of the cutting element, viz. cuts, without correspondingly claiming more space and/or weight.

According to the invention, this object is achieved by means of a surgical instrument described herein.

From said configuration according to the invention of the surgical instrument the following further advantages can be derived, for example:

Without an additional gearwheel the gear ratio between the trigger element and the pinion is increased.

Rotation of the pinion results from a rack fixed (to the handle) which can be flexibly attached, thus increasing the adaptability of the coupling mechanism according to the invention.

The travel of a rack can be determined from the product of the circular constant pi as well as the diameter and the rotational speed of the pinion, the rack being intended to be about as long as a travel. According to the invention, thus the travel is doubled while the diameter of the pinion remains constant and also the rotational speed remains constant, the rack having to be only half as long as the travel. Alternatively, with a constant stroke the space required and the swivel movement required at the trigger element (handle) can be significantly reduced.

The subject matter of the invention consequently is a surgical instrument comprising a shaft portion which at its distal end/end area at least partly houses/supports an axially movable cutting element such as a blade/a knife/an HF cutting unit etc. connected/operable via a (pull/push) rod. The surgical instrument further includes a handle receiving the shaft portion (at the proximal end/end area thereof) on which an e.g. lever-type trigger element (handle) for the cutting element is movably arranged and in which a coupling mechanism is accommodated which converts a (partial) rotation of the preferably lever-type trigger element into an axial movement of the cutting element via the (pull) rod with a pinion or a friction roller being interposed.

According to the invention, the coupling mechanism is designed so that the rotation/swivel movement of the trigger element about the swivel axis thereof causes rotation of the pinion/friction roller about its central axis and, in addition, produces a translational/axial movement of the central axis of the pinion/friction roller (in the direction of rotation thereof). Said two components of movement, i.e. the rotation of the pinion/central axis about the central axis and translation of the pinion/central axis add up so as to extend the travel path of the cutting element in total. The travel path resulting from the rotation of the pinion/friction roller can be varied via the diameter of the pinion/friction roller. The travel path resulting from the translation of the central axis of the pinion/friction roller can be varied via the length and the pivot of the trigger element (relevant/active lever length). Thus, the surgical instrument is equipped with a plurality of components/parameters/setting options to influence the travel path of the cutting element with smallest possible space and weight required in a way extending or reducing the same.

In other words, the afore-mentioned functional principle can be structurally realized, for example, by the handle-side trigger element (handle) being in the form of a centrally (somewhere in the middle) pivoted (actuating) lever having a pinion/friction roller freely supported (movably in the longitudinal lever direction) at the free end of the lever-shaped trigger element (opposite to the actuating end of the trigger element), the pinion/friction roller in turn being clamped between an immovable roll-off raceway (e.g. fixed to the handle housing) such as e.g. a fixed rack, and a roll-off raceway preferably movable in parallel thereto such as a rack movable (in parallel). When the lever is swiveled and thus the central axis of the pinion/friction roller is translationally moved between the two racks, the pinion/friction roller rolls off the fixed roll-off raceway and drives the movable roll-off raceway which is coupled to the cutting element via the (pull/push) rod at a particular transmission ratio corresponding to the active lever arm length and to the pinion/friction roller diameter. By interposing the pinion/friction roller between the (manually operable) trigger element and the (push/pull) rod the displacing path of the (push/pull) rod can be varied by varying the pinion/friction roller diameter, while the trigger/actuating distance of the trigger element (pivot angle) remains constant.

Basically, an extension of the displacing distance of the (push/pull) rod can be obtained, as a matter of course, by the lever aim of the trigger element being simply extended. However, this would entail a larger constructional design of the handle housing so as to (partly) accommodate the extended trigger element in the same. By interposing the pinion/friction roller, however, an additional transmission ratio may be integrated in the coupling mechanism, thus enabling extension of the trigger element to be prevented. In this way, it is no longer necessary to (substantially) enlarge the handle housing.

In a preferred embodiment, the axial movement of the cutting element, i.e. the length of the travel path and, resp., the length of the cut at a patient, exceeds the axial movement carried out by the central axis of the pinion and directly caused by the trigger element. In this way, the user is able to produce, by a short actuating movement, a cut which is long compared to said movement. Apart from the afore-mentioned advantages, this has a positive effect on the force to be applied by the user. Surgical operations frequently take several hours, therefore any saving of force on the side of the user/surgeon resulting from an increase in the operating comfort minimizes the risk of failure and thus is also relevant to safety aspects.

In particular due to the fact that a tooth area of the pinion engages in a (handle) fixed rack, while simultaneously a different/opposite tooth area of the pinion engages in a rack fixed to the cutting element/movable in parallel/movable relative to the handle, the instrument is achieved to be highly compact.

An advantageous configuration according to the invention of the present invention excels by the fact that the axial movement of the cutting element is substantially twice as large as the axial movement carried out by the central axis of the pinion. Accordingly, the diameter of the pinion and the circular arc segment traced by the pinion-side end of the trigger element are adapted to each other such that the actuating distance of the trigger element, viz. the movement to be carried out by the user for a cut, is half as large as the actual cut. This ratio of substantially 1:2 takes the target of construction space optimization as well as of force reduction sufficiently into account, while it further produces such operability of the instrument that the user has an intuitive feeling for the length of the cut.

Especially when the axial movement carried out by the central axis of the pinion substantially corresponds to the axial movement of a grip area of the trigger element, compact arrangement of the coupling mechanism is ensured. The grip/actuating area of the (lever-shaped) trigger element is provided at the lower end of the trigger element (relative to the central bearing thereof), i.e. distant from the pinion. When its axial movement, or in other words the axial part of its movement of rotation, substantially corresponds to the axial movement of the central axis of the pinion, this means that the point about which the trigger element rotates is centrally arranged. Said point of rotation of the trigger element is preferably configured at an edge of the handle (close to the handle housing). Thus, substantially the one half of the trigger element is arranged inside the handle, while the other half is arranged outside the handle. In this way, the trigger element has no projection either in the one direction or in the other direction, which has a positive effect on the dynamics thereof.

In an advantageous embodiment of the invention, the tooth area of the pinion engaging in the fixed rack after a half turn of the pinion engages in the movable rack. In other words, the same tooth area alternately engages in the stationary fixed rack and in the movable rack driven by the pinion. It is resulting herefrom that at the time when one tooth area engages in the one rack, another one engages in the other rack. In this way, in minimum construction space around the pinion different tooth engagements are realized, thus allowing the space required for the coupling mechanism to be reduced. Depending on the embodiment, the longitudinal axis of the respective racks is variable as to their orientation as long as they extend tangentially relative to the pinion (and preferably are also aligned in parallel to each other).

According to the invention, the pinion includes two concentric portions of different diameters along its central axis, with the one portion engaging in the fixed rack while the other portion engages in the movable rack. The different diameters result in an additional transmission stage of the coupling mechanism. Depending on the application, the respective portion can be flexibly adapted to the prevailing requirements. Thus, the diameter deviation of the respective portions can be freely configured.

It is especially advantageous when the pinion is freely movable in the height direction of the surgical instrument (and, resp., substantially along the lever-shaped trigger element) relative to the trigger element, while it is fixedly coupled to the trigger element in the axial direction of the shaft/the shaft portion (and, resp., transversely to the lever-shaped trigger element). The free mobility in the height direction is realized by means of a fork-shaped bearing bracket (along the lever-shaped trigger element) which includes two slit-shaped recesses (bearing forks) for receiving the central axis of the pinion. By means of the facing oblong slits a relative movement in the afore-defined height direction is realized. As the width of the slits substantially corresponds to the diameter of the central axis of the pinion (is slightly wider), the fixed coupling of the central axis of the pinion in the axial direction is ensured. In this way, bearing of the pinion on the lever-shaped trigger element is enabled in a confined space with two degrees of freedom— viz. rotation about the central axis of the pinion and translation of the pinion in the height direction (i.e. along the lever-shaped trigger element).

As soon as the fixed rack is configured to be integral with the handle, the manufacture of the handle which is advantageously carried out by injection molding, is realized in a time-efficient and cost-efficient manner. Alternatively, it is also possible to manufacture the fixed rack as a separate component and to connect it to the handle e.g. via adhesive closure (or by rivets or clips). This helps increase the modularity of the surgical instrument.

In another advantageous embodiment of the present invention, the pinion has toothings of different diameter/ different geometry so that the axial movement of the cutting element can be varied by means of a switching movement of the pinion along its central axis. As afore-explained, the linear movement transmitted from the pinion to the movable rack and thus to the cutting element varies with the diameter of the pinion. By means of the configuration of different toothing geometries which, when they are engaging, engage in the respective two racks, paired with the switching movement thus different gear ratio stages are realized in a same construction space in the height direction and the axial direction of the handle. By means of said option of switching different pinion sizes, the flexibility of the surgical instrument is further increased.

In addition, it is mentioned that the shaft portion of the surgical instrument according to the invention in one embodiment is prepared to perform a movement of rotation about its longitudinal axis. Said movement of rotation is supported e.g. by the coupling mechanism.

In another advantageous embodiment of the surgical instrument according to the invention, the movable rack extends, on the one hand, in the axial direction of the shaft portion and, on the other hand, at least partially in the circumferential direction about the shaft portion. In the afore-mentioned direction of rotation of the shaft portion about its longitudinal axis, this enables the pinion to continue engaging in the movable rack. The movement of rotation may extend in an angular span of up to 360°. Thus, a highly flexible cutting movement is possible. As during said rotation the pinion continues being in contact with the movable rack, the surgical instrument has a robust rotation transmission mechanism.

Especially when between the trigger element and the pinion an additional coupling unit is arranged via which relative displacement between the coupling mechanism and the cutting element is allowed while the position of the trigger element is unchanged, a cutting movement tailored to the respective application can be realized. Thus, actuation of the additional coupling unit causes the cutting element to be displaced relative to the coupling mechanism while the position of the trigger element is unchanged.

Also, it is advantageous when the coupling mechanism houses a return spring, preferably of the type of a tension spring, a compression spring or a torsion spring, which is prepared to return the cutting element to its home position after actuation. Thus, no force has to be applied by the operating surgeon in order to move the trigger element and the cutting element to the home position after a cutting movement. In the case of configuration by means of a tension spring, said tension spring is arranged at the movable rack, the pinion or the trigger element in the area of the pinion. In the case of configuration by means of a compression spring, said compression spring is arranged distally relative to the movable rack, the pinion or the trigger element in the area of the pinion. Further, the compression spring may also be arranged around the shaft portion. Another configuration of the return spring is a torsion spring. Said torsion spring preferably has to be arranged around the axis of rotation of the trigger element in order to exert a force on the same in the case of returning the cutting element.

The inventive idea moreover comprises the configuration of the pinion according to the invention in a conventional scissors-type gripping instrument in which a small lever or a sliding component drives the pinion to move the cutting element.

Advantageously, the two concentric toothing portions of the pinion are configured to be integral with and, resp., relative to each other. Alternatively, the two concentric toothing portions are in the form of two components separate from each other which further preferred are separated from each other by a gap.

Within the scope of the invention, advantageously the toothing portion having the larger diameter is intended to engage in the fixed rack, whereas the toothing portion having the smaller diameter engages in the movable rack. In this way, the revolving movement is achieved to be transmitted via a first angular portion of the larger gearwheel/ toothing portion to an increased revolving movement of a second angular portion of the smaller gearwheel/toothing portion, which renders this embodiment especially suited for particularly long shafts.

BRIEF DESCRIPTION OF THE DRAWING FIGURES

Hereinafter, the invention shall be illustrated in detail by way of a preferred example embodiment with reference to the accompanying figures, wherein.

DETAILED DESCRIPTION

Figure 1:
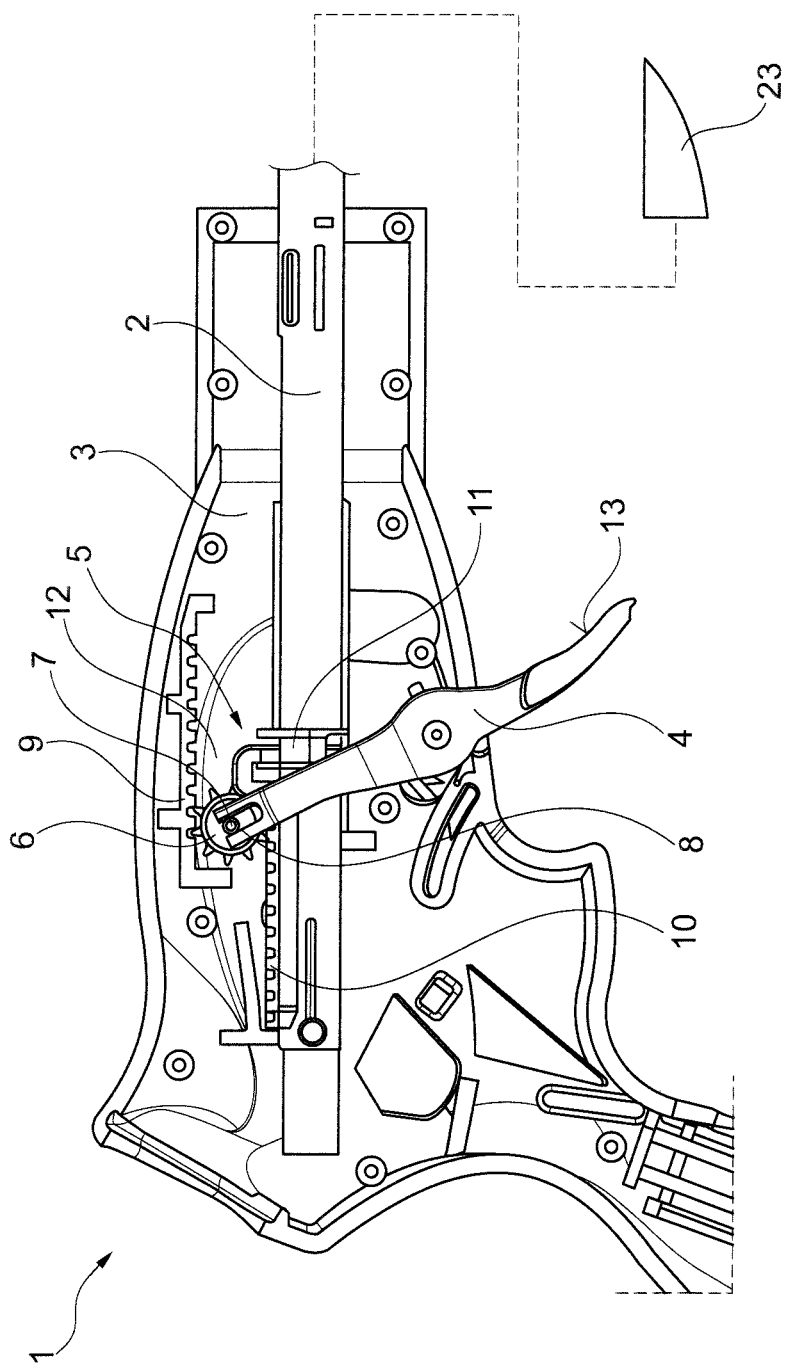
FIG. 1 shows a sectional view across a handle along the axial direction of a surgical instrument according to the invention in a first condition.

The figures are merely schematic and serve exclusively for the understanding of the invention. The same elements are provided with the same reference numerals.

FIG. 1 illustrates a surgical instrument 1 of the minimally invasive design, for example, comprising a shaft portion (instrument shaft) 2 extending in the distal direction which at least partly houses an axially movable cutting element 23 at its distal end. The cutting element 23 and the coupling thereof to the shaft portion 2 is shown merely schematically. In the real embodiment, the cutting element 23 is rigidly and linearly coupled. The instrument 1 has a pistol-type handle 3 at which a lever-type trigger element 4 via which the cutting element 23 is actuatable is rotatably disposed. The trigger element 4 actuatable by a user, such as a surgeon, via a grip area 13 (of the trigger element 4) is operatively connected to a coupling mechanism 5 at its end facing away from the grip area 13. The coupling mechanism 5 converts the partial rotation of the trigger element 4 produced by the user into a linear movement/an axial movement of the cutting element 23 with the interposition of a pinion 6.

For this purpose, according to the invention the coupling mechanism 5 includes two racks, viz. a rack 9 fixed (to the handle) and a rack 10 movable relative to the handle (and thus displaceable) which are aligned in parallel to each other. The pinion 6 in the present embodiment engages in the fixed rack 9 with a first upper tooth portion, while it engages in the movable rack 10 with a second lower tooth portion.

In order to enable the pinion 6 to rotate while it simultaneously engages in two different racks 9, 10, the central axis 7 of the pinion 6 is configured to be movable in the axial direction (i.e. along the racks 9, 10). This results in the fact that an actuation of the trigger element 4 causes rotation thereof about the bearing point thereof which, in turn, moves the pinion 6 that is operatively connected/coupled to the trigger element 4, on the one hand in the axial direction and, on the other hand, rotates the pinion about its central axis 7 while it interacts with the respective racks 9, 10.

The coupling mechanism/area 5 according to the invention thus is configured so that the rotation of the trigger element 4 causes rotation of the pinion 6 about its central axis 7 and additionally causes an axial movement of the central axis 7.

The fixed rack 9 is arranged to be stationary, which results in rotation of the pinion 6 in the direction of the arrow 12. The linear movement of the movable rack 10 is composed of two parts:

The first part results from the axial movement of the central axis 7 of the pinion 6 which is caused exclusively by the trigger element 4.

The second part results from the rotation 12 of the pinion 6 driving the movable rack 10. Said rotation 12 is produced by the stationary fixed rack 9 in interaction with the axial movement of the central axis 7.

In the present example embodiment, the two parts are approximately equally weighted.

The first part is determined by the angular span that is covered by the grip area 13 when triggered by a user. Said angular span relates, apart from the movement of the user, to the length of the trigger element 4 and the bearing point thereof. The bearing point is configured in an edge area of the handle 3 and is arranged approximately centrally along the longitudinal axis of the lever-type trigger element 4.

At the end of the trigger element 4 facing away from the grip area 13 a (fork-shaped) bearing bracket 8 is configured. The latter on the one hand provides for the axial guiding of the central axis 7, on the other hand it enables, due to its oblong slits, the rotation of the trigger element to produce a linear movement of the central axis 7. That is to say, the bearing bracket 8 is configured such that it admits two degrees of freedom of the central axis 7, i.e. the one in the height direction of the surgical instrument 1 and the rotation along the central axis 7. Said rotation is preferably ensured via an additional bearing of the central axis 7 to guarantee an uniform, low-wear rotation.

A connecting member 11 establishes a connection between the movable rack 10 and the cutting element 23 arranged at the distal end. The connecting member 11 is in the form of a bracket and preferably connects the movable rack 10 to a (pull/push) rod/actuating rod which in turn rigidly guides the cutting element 23. Said actuating rod preferably extends inside the shaft portion 2.

The connecting member 11 may also be referred to as cutter collar. Preferably, it houses a radial bearing to enable possible rotation of the cutting element about the longitudinal axis of the shaft portion.

Figure 2:
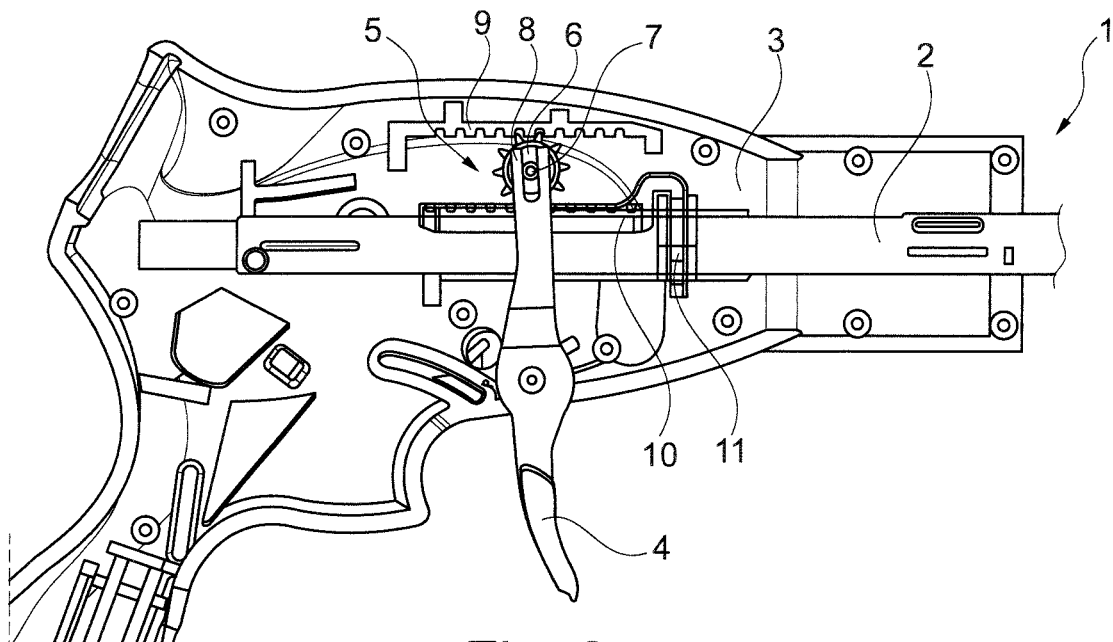
FIG. 2 shows the handle from FIG. 1 in a condition in which a trigger element has been partially actuated.

FIG. 2 illustrates the surgical instrument 1 in a second condition. In this Figure as well as in FIG. 3 the schematic view of the cutting element 23 is dispensed with. The trigger element 4 has been swiveled in the proximal direction at its grip area 13 around a particular angular span around its bearing point. On the opposite side of the bearing point, this causes a movement of the central axis 7 of the pinion 6 in the distal direction. In the present condition, the pinion stands approximately centrally in the fixed rack 9. Herefrom it follows that the cutting element 23 has covered approximately half of its travel.

Complying with the invention idea, the connecting member 11 has covered a larger distance than the central axis 7 in the axial direction. This follows from the fact that the pinion 6, in addition to the axial movement of its central axis 7, now engages in the movable rack 10 approximately centrally, whereas in FIG. 1 it has still been provided at the distal end thereof. The distance of the cutting element 23 covered thus is composed of the distance of the central axis 7 added to the distance of the relative position between the pinion 6 and the movable rack 10 which is also referred to as cutter rack.

In order to guarantee the two different drives of the fixed rack 9, viz. the axial movement of the central axis 7 and the rotation of the pinion 6, the receiving slits of the fork-type bearing bracket 8 are required. Comparing the position of the central axis 7 in FIG. 2 to that of the central axis in FIG. 1, it is noticed that due to the degree of freedom of the central axis 7 said position has migrated in the height direction within the receiving slit.

Figure 3:
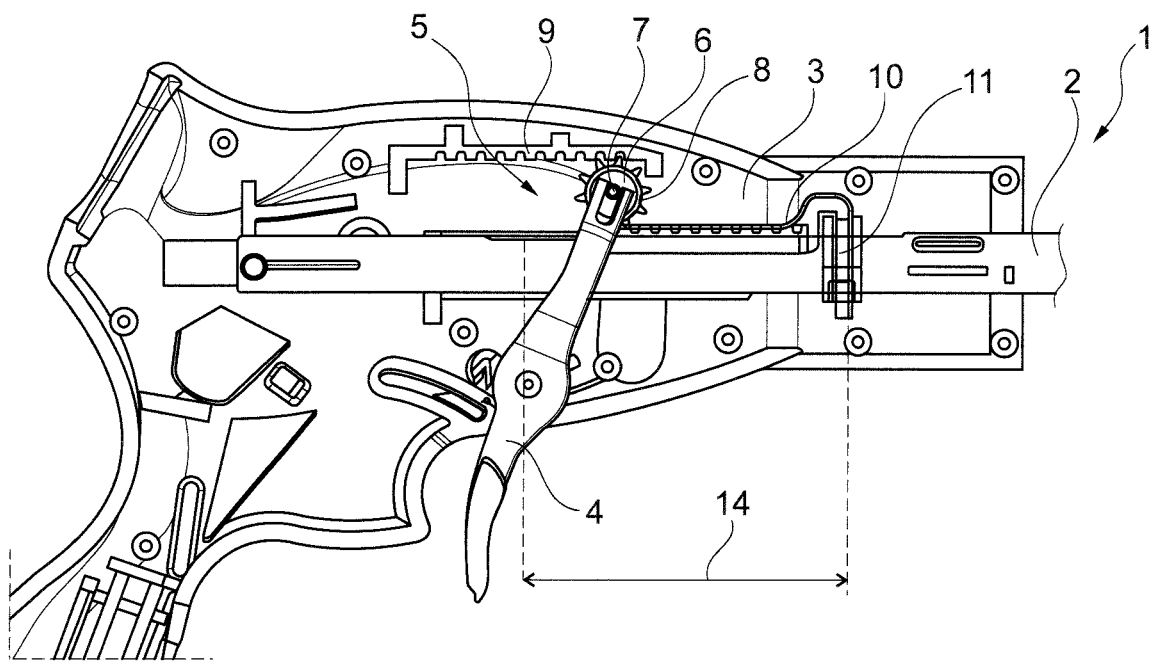
FIG. 3 shows the handle from FIG. 1 in a condition in which the trigger element has been completely actuated.

In FIG. 3, the surgical instrument 1 is illustrated in a condition in which the entire travel path, i.e. the entire stroke, of the cutting element 23 has been covered. Thus, the pinion 6 is provided at the distal end of the fixed rack 9.

A distance 14 shown in FIG. 3 schematically illustrates the distance of the connecting member 11 covered between the initial condition in FIG. 1 and the final condition in FIG. 3. Said distance exceeds the distance covered of the central axis 7 which is approximately similar to the length of the fixed rack 10.

The fixed rack 9 and the movable rack 10 take substantially the same length. Thus, a minimum required construction space is realized. Moreover, this offers the advantage that the two racks 9, 10 are to be designed as same parts, thus increasing the economic efficiency in manufacture.

Figure 4:
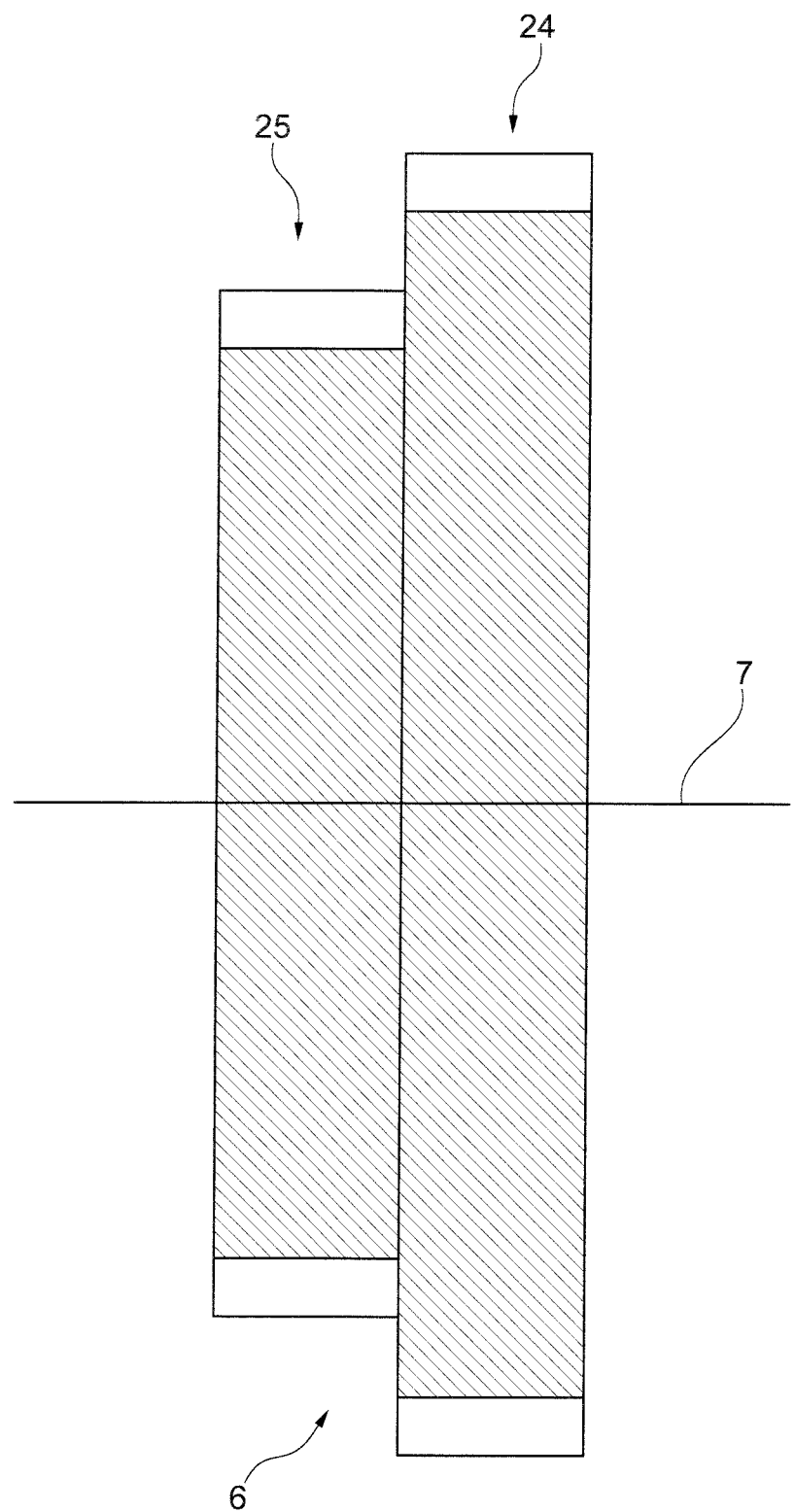
FIG. 4 shows a schematic view of a pinion having two toothing portions.

FIG. 4 illustrates a pinion 6 having two toothing portions 24, 25 of different diameters. Said portions 24, 25 may be configured to be integral with or separate from each other. While the portion 24 is prepared to engage in the fixed rack 9, the portion 25 is prepared to engage in the movable rack 10. This allows to ensure a sufficient travel movement of the cutting element 23 in the case of instruments 1 having a long shaft 2.

The invention claimed is:

1. A surgical instrument comprising a shaft portion which at least partly houses or holds an axially movable cutting element, and comprising a handle which receives the shaft portion and on which a manually actuatable trigger element for the cutting element is arranged movably, as well as comprising a coupling mechanism which converts a movement of the trigger element into an axial movement of the cutting element, wherein the coupling mechanism has a pinion which is interposed in the train of movement provided by the coupling mechanism such that the movement of the trigger element produces rotation of the pinion about its central axis and additionally a translational movement of the central axis along the direction of movement of the cutting element itself, wherein a tooth area of the pinion engages in a fixed rack, while another tooth area of the pinion engages in a movable rack, wherein the pinion includes two concentric toothing portions of different diameters along its central axis, with the one toothing portion engaging in the fixed rack, while the other toothing portion engages in the movable rack, and the movable rack extends in the axial direction of the shaft portion and at least partly in the circumferential direction around the shaft portion so that the pinion engages in the movable rack even in the case of rotation of the shaft portion about its longitudinal axis.

2. The surgical instrument according to claim 1, wherein the axial movement of the cutting element exceeds the translational movement or axial movement of the central axis performed by the central axis of the pinion and caused by the trigger element.

3. The surgical instrument according to claim 1, wherein the axial movement of the cutting element is substantially twice as large as the axial movement performed by the central axis of the pinion.

4. The surgical instrument according to claim 1, wherein the axial movement performed by the central axis of the pinion substantially corresponds to the axial movement of a grip area of the trigger element.

5. The surgical instrument according to claim 1, wherein the pinion is freely movable in the height direction of the surgical instrument relative to the trigger element, while in the axial direction it is rigidly coupled to the trigger element.

6. The surgical instrument according to claim 1, wherein the fixed rack is configured to be integral with the handle.

7. The surgical instrument according to claim 1, wherein the coupling mechanism houses a return spring, which is prepared to return the cutting element to its home position after actuation.

8. The surgical instrument according to claim 1, wherein the two concentric toothing portions of the pinion are formed to be integral with each other.

9. The surgical instrument according to claim 1, wherein the two concentric toothing portions are configured as two components separate from each other and are separated from each other by a gap.

10. The surgical instrument according to claim 1, wherein the toothing portion having the larger diameter engages in the fixed rack, while the toothing portion having the smaller diameter engages in the movable rack.

* * * * *